United States Patent
Levesque et al.

(10) Patent No.: US 6,393,901 B1
(45) Date of Patent: May 28, 2002

(54) PRESSURE CELL FOR SUBJECTING AN ABSORBENT ARTICLE TO COMPRESSIVE STRESS DURING A LIQUID-ABSORBENCY TEST

(75) Inventors: Yvon Levesque, Montreal; Jean-Marc Beliveau, Ville d'Anjou, both of (CA)

(73) Assignee: Johnson & Johnson, Inc., Montreal (CA)

( * ) Notice: Subject to any disclaimer, the term of this patent is extended or adjusted under 35 U.S.C. 154(b) by 0 days.

(21) Appl. No.: 08/318,023

(22) Filed: Oct. 4, 1994

(51) Int. Cl.[7] .............................. G01N 5/02; G01N 25/56
(52) U.S. Cl. ............................................ 73/73
(58) Field of Search .......................... 73/73, 159, 74, 73/75, 76, 77

(56) References Cited

U.S. PATENT DOCUMENTS

| | | | | |
|---|---|---|---|---|
| 2,667,782 A | * | 2/1954 | Shea | 73/37 |
| 2,907,203 A | | 10/1959 | Langmead | 73/73 |
| 3,419,964 A | | 1/1969 | Hennigan | 33/174 |
| 3,845,783 A | | 11/1974 | De Lepeleire | 137/504 |
| 3,876,138 A | | 4/1975 | Dean, Jr. | 236/49 |
| 3,886,057 A | | 5/1975 | Bredweg | 204/195 |
| 3,952,584 A | * | 4/1976 | Lichstein | 73/73 |
| 4,535,635 A | * | 8/1985 | Claren et al. | 73/756 |
| 4,548,072 A | | 10/1985 | McAndless | 73/159 |
| 4,573,335 A | * | 3/1986 | Persson | 72/63 |
| 4,655,076 A | * | 4/1987 | Weihe et al. | 73/73 |
| 5,361,627 A | * | 11/1994 | Levesque | 73/73 |

FOREIGN PATENT DOCUMENTS

| | | | | |
|---|---|---|---|---|
| RU | 941-622 | * | 7/1982 | 73/37 |
| SU | 1640612 | * | 4/1991 | 73/7 |

* cited by examiner

*Primary Examiner*—Hezron E. Williams
*Assistant Examiner*—Paul D. Amrozowicz

(57) ABSTRACT

A pressure cell for subjecting a liquid-absorbent article to static compression; employed for conducting liquid-absorbency test procedures. The pressure cell includes an inflatable bag which compresses the absorbent article while conforming to its tri-dimensional configuration in order to achieve a uniform pressure distribution. The pressure cell is particularly suitable for conducting tests on non-planar, anatomically shaped absorbent articles or test samples that undergo a change in volume upon wetting. The invention also extends to a method for conditioning a liquid-absorbent article by the application of pressure during experimental liquid-absorbency procedures.

14 Claims, 1 Drawing Sheet

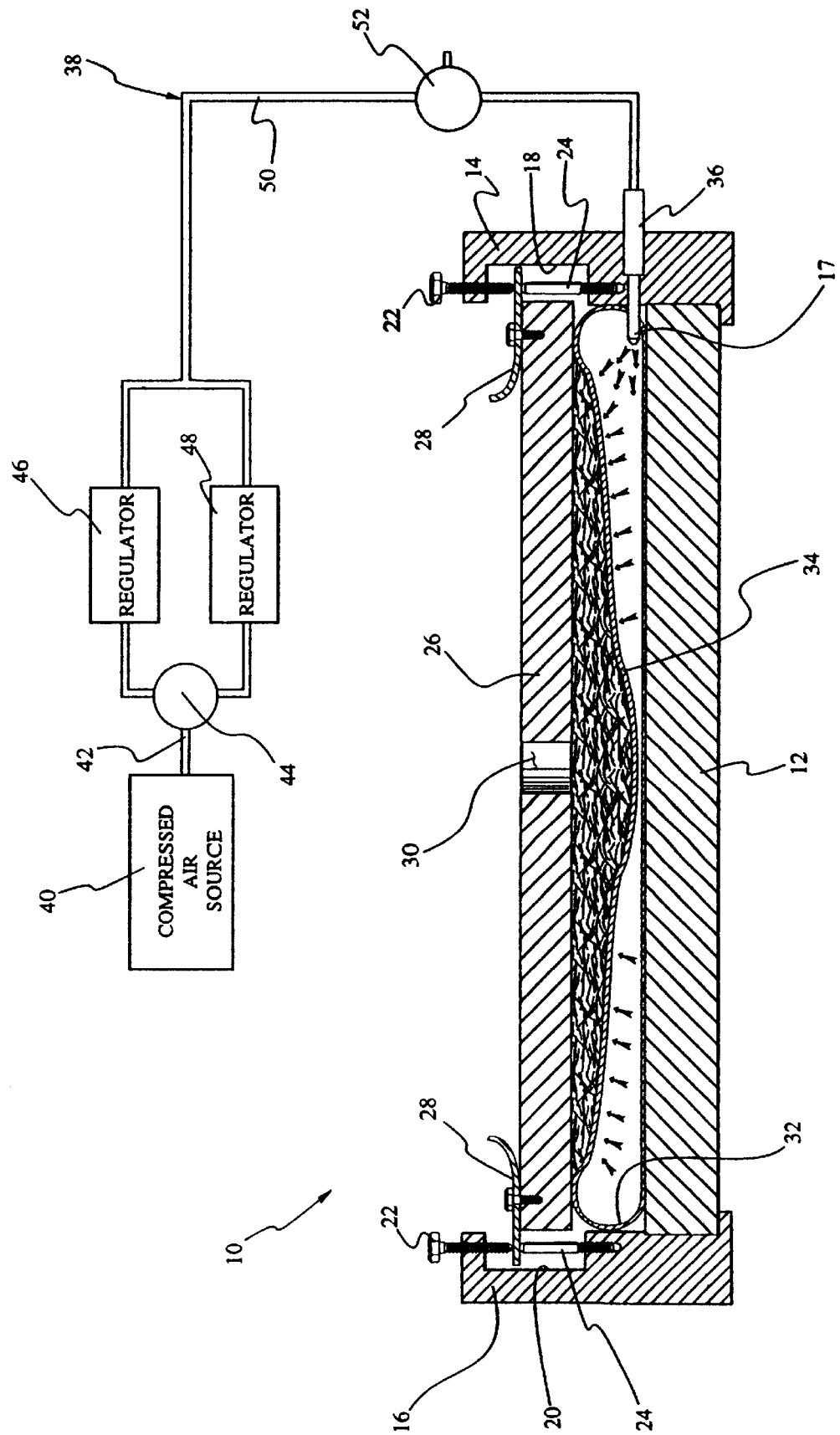

PRESSURE CELL FOR SUBJECTING AN ABSORBENT ARTICLE TO COMPRESSIVE STRESS DURING A LIQUID-ABSORBENCY TEST

FIELD OF THE INVENTION

The invention relates to an instrument for subjecting a liquid-absorbent article to controlled pressure during experimental liquid-absorbency procedures. Pressure is exerted on the sample by the intermediary of a flexible membrane to achieve a more uniform pressure distribution. The invention also extends to a method for conditioning a liquid-absorbent article by the application of pressure for conducting liquid-absorbency tests.

BACKGROUND OF THE INVENTION

Manufacturers of disposable absorbent articles such as sanitary napkins, diapers, adult briefs, urinary pads, wound dressings, nursing pads, tampons, or desiccants to keep goods dry during shipping and storage typically perform numerous absorbency tests on proposed new designs to attain full comprehension of their behaviour. It is often useful to test the absorbent properties of such articles under pressure. Generally, this is accomplished by placing the absorbent article to be tested between two rigid plates that are vertically movable one with relation to the other. Dead weights are then placed on the upper plate to obtain the desired pressure level. An access port in the upper plate allows the laboratory technician to feed test liquid to the sample or to insert in the pressure cell the probe of a measurement device.

The procedure described above is suitable if the sample has a planar configuration and remains dimensionally stable when wetted. This pressure cell, however, is inapt for handling anatomically shaped absorbent products because the pressure distribution created by the rigid plates is far from being uniform. The same problem is observed with most fluff-based products that collapse when placed in contact with liquid. It will become apparent that once the test liquid is delivered to the sample, the region surrounding the point of impact abruptly shrinks which causes a pressure depletion in that area. The reverse problem is observed with materials containing sphagnum moss or superabsorbents that swell up upon absorption of liquid. In those cases, the injection of liquid in the sample causes a pressure concentration in the wetted zone.

Pressure discrepancies along the sample should be reduced as much as possible, otherwise the test results may be corrupted. Accordingly, it is desirable to provide a pressure cell capable of subjecting absorbent samples that are non-planar or undergo dimensional changes upon wetting to more uniform pressures during liquid-absorbency tests.

OBJECTS AND SUMMARY OF THE INVENTION

An object of the invention is a pressure cell for conducting liquid-absorbency experimental procedures, which is capable of subjecting the sample to a more uniform pressure than prior art devices.

Another object of the invention is an improved method for conditioning a liquid-absorbent article by the application of pressure during experimental liquid-absorbency procedures.

As embodied and broadly described herein, the invention provides a pressure cell for conditioning a liquid-absorbent article by the application of compressive stress thereon during a liquid-absorbency test (For the purpose of this specification, "liquid-absorbency test" shall mean an experimental procedure for ascertaining a quality of the absorbent article that has connection, relation or reference to absorption of liquid. The experimental procedure may or may not involve a transfer of liquid to the sample under observation.), said pressure cell comprising:

an abutment member;

a variable volume chamber including a flexible membrane, said abutment member and said flexible membrane defining therebetween a three-dimensional space for receiving the liquid-absorbent article, said variable volume chamber being inflatable by injection of pressurized fluid therein to cause said flexible membrane to compress the liquid-absorbent article while conforming thereto, whereby said pressure cell allows to conduct a liquid-absorbency test on the liquid-absorbent article in a compressed condition between said flexible membrane and said abutment member.

In a preferred embodiment, the pressure cell comprises a frame made of two rigid plates vertically spaced from one another. A bag of supple plastic material, polyethylene for example, is laid on the bottom plate. The absorbent article to be tested is placed between the flexible bag and the upper plate, and the bag is inflated by injection of compressed air. In the inflated condition, the bag compresses the absorbent article against the upper plate while conforming to its tri-dimensional configuration to achieve a uniform pressure distribution. It will also be apparent that the flexible bag manifests a dynamic adaptive behaviour when the sample undergoes dimensional changes upon absorption of liquid. For instance, if the sample locally swells-up or shrinks, the bag follows the shape evolution to maintain the pressure loading substantially uniform.

As embodied and broadly described herein, the invention also provides a method for conditioning a liquid-absorbent article by the application of pressure to the liquid-absorbent article during a liquid-absorbency test, said method comprising the steps of:

placing the liquid-absorbent article between an abutment member and a flexible membrane forming a wall of an inflatable bag;

injecting pressurized fluid in said bag to cause said flexible membrane to compress the liquid-absorbent article while conforming thereto, whereby allowing to conduct a liquid-absorbency test on the liquid-absorbent article while maintaining the liquid-absorbent article in a compressed condition between said flexible membrane and said abutment member.

BRIEF DESCRIPTION OF THE DRAWING

The annexed drawing is a vertical cross-sectional view of a pressure cell constructed in accordance with the invention.

DESCRIPTION OF A PREFERRED EMBODIMENT

With reference to the annexed drawings, the pressure cell designated comprehensively by the reference numeral 10 comprises a rigid frame for holding an absorbent article during a test conducted for measuring a liquid-absorbent property. The frame includes a lower, horizontally extending rigid plate 12 that constitutes a base for supporting the pressure cell on a table or on a stand and a pair of holding bars 14, 16, vertically projecting from respective longitudinal extremities of the plate 12. The holding bars 14 and 16 are provided with recesses 18, 20, that accommodate an upper stop member 22 and a lower stop member 24. The stop members are in the form of screws threaded in the holding bars 14, 16 to form vertically spaced apart abutments, as it will be described later.

An upper horizontally extending rigid plate 26, vertically spaced apart from the lower plate 12, is slidingly mounted between the holding bars 14 and 16. The upper plate 26 is held in place by slidable gates 28 that fit between the abutments formed by the tips of vertically aligned screws 22 and 24.

The upper plate 26 is provided with a port 30 in the form of a circular aperture allowing to access the interior of the pressure cell. Typically, the port 30 is used for feeding liquid to the absorbent article that is being tested or to introduce in the pressure cell the probe of an instrument to perform the liquid-absorbency measurement. An example of such instrument is described in the U.S. patent application Ser. No. 996,476 in the name of Johnson & Johnson Inc. filed on Dec. 31, 1992. This instrument measures the capillary attraction developed at the surface of an absorbent body and comprises a probe of fritted glass providing an array of capillaries passageways in fluid communication with the interior of the closed chamber completely filled with liquid. A pressure sensor mounted to the closed chamber observes the liquid pressure therein. When the probe is placed in contact with an absorbent body, the capillary attraction exerted on the liquid in the probe capillaries by the porous network of the absorbent body is transmitted through liquid medium in the closed chamber to the pressure sensor. The pressure data thus obtained reflects the state of dryness of the absorbent body surface.

When the above described instrument is used with the pressure cell 10, the probe of the instrument is inserted through the port 30 to contact the upper surface of the absorbent article that is being tested. Since the absorbent article is maintained in a compressed condition, as will be described below, it is desirable to hold the probe stationary in the port 30 so as to prevent the probe from being pushed out from the pressure cell by the absorbent article. At this end, any suitable clip or fastener may be used to hold the probe in place during the test procedure. Another possibility is to manufacture the probe with a shape complementary to the configuration of port 30 so the probe can be friction locked in the access port.

The agency to compress the sample within the pressure cell 10 is a flexible bag 32 forming a variable volume chamber that can be inflated by injection of pressurized fluid. Most preferably, the bag 32 is made from 0.05 millimeters (mm) thick polyethylene and has a sample engaging wall formed by a flexible membrane 34. In the embodiment illustrated in the drawings, the membrane 34 is actually the portion of the bag 32 that is co-extensive with the sample being tested. In a variant, the flexible membrane in the form of a single sheet may be used which is peripherally bonded to the rigid plate 12. In such an embodiment, the variable volume chamber is defined between a rigid wall (plate 12) and the single flexible sheet.

A short conduit 36 passing through the vertical holding bar 14 and penetrating within the bag 32 establishes a fluid path for supplying pressurized fluid, such as air, to the variable volume chamber. Outside the pressure cell, the conduit 36 connects with an air supply system 38 comprising a compressed air source 40 of any suitable type that is capable of providing low pressure air such as at a few pounds per square inch (psi). The compressed air source 40 supplies pressurized air via a conduit 42, a two-position selector mechanism 44 and either one of regulators 46 and 48 to a common conduit 50 connecting with the conduit 36. The common conduit 50 contains a bleed valve 52 for venting outside the air supply system 38, thus depleting the pressure exerted on the sample.

The regulators 46 and 48 of the pneumatic system are precision devices that can be preset to supply two predetermined operating pressures, for example 0.1 psi and 1.5 psi or higher, in order to measure liquid-absorbent properties under those typical pressures. Note that the dual pressure air supply is a convenient way of measuring wetback resistance of the sample. Briefly stated, this is performed by discharging liquid on the sample maintained under low pressure condition and then switching the selector 44 to the high pressure mode and then observing the tendency of the liquid to egress the absorbent article.

To perform a test on the absorbent properties of the sample, the pressure cell is prepared by removing the top plate 26 in order to expose the membrane 34. The absorbent article to be tested in then placed on the membrane 34 and the top plate 26 is put back in place. The stop members 28 are laterally extended to fit between the screws 22 and 24 and thus lock the plate against vertical movement. It will be apparent that the ability of the screws 22 and 24 to move vertically allow to adjust the locked position of the plate 26 with relation to the plate 12 according to the thickness of the sample. The pneumatic system 38 is then activated to inflate the bag 32 at the selected pressure value. The membrane 34 urges the absorbent article against the upper plate 26, while conforming to the tri-dimensional shape of the absorbent article so as to provide a uniform pressure distribution. If the absorbent article exhibits dimensional changes such as shrinking or swelling due to absorption of liquid, the membrane 34 dynamically adapts to the change of shape to maintain the pressure as uniform as possible.

Finally, the probe of the measuring instrument is placed in the port 30 and locked in place. The testing procedure is carried out as required.

The scope of the present invention is not limited by the description, examples and suggestive uses herein, as modifications can be made without departing from the spirit of the invention. Thus, it is intended that the present application covers the modifications and variations of this invention provided that they come within the scope of the appended claims and their equivalents.

We claim:

1. A pressure cell for conditioning a liquid-absorbent article by the application of compressive stress thereon during a liquid-absorbency test, said pressure cell comprising:

an abutment member;

a variable volume chamber including a flexible membrane, said abutment member and said flexible membrane defining therebetween a three-dimensional space for receiving the liquid-absorbent article, said variable volume chamber being inflatable by injection of pressurized fluid therein to cause said flexible membrane to compress the liquid-absorbent article while conforming thereto, whereby said pressure cell allows to conduct a liquid-absorbency test on the liquid-absorbent article in a compressed condition between said flexible membrane and said abutment member.

2. A pressure cell as defined in claim 1, comprising a port for feeding test liquid to the liquid-absorbent article.

3. A pressure cell as defined in claim 1, comprising a port for receiving a probe of an instrument for measuring a liquid-absorbent characteristic of the liquid-absorbent article.

4. A pressure cell as defined in claim 1, wherein said variable volume chamber includes a bag of flexible material, said flexible membrane constituting a wall of said bag.

5. A pressure cell as defined in claim 4, comprising a conduit connected to said bag for supplying pressurized fluid thereto.

6. A pressure cell as defined in claim 1, comprising a pressure regulator in a fluid path with said variable volume chamber for regulating a pressure in said variable volume chamber.

7. A pressure cell as defined in claim 6, comprising a plurality of pressure regulators capable of being individually set in a fluid path with said variable volume chamber, each pressure regulator being capable of maintaining a pressure in said variable volume chamber at a preset level.

8. A pressure cell as defined in claim 1, wherein said abutment member includes a rigid generally horizontal plate.

9. A pressure cell as defined in claim 8, wherein said plate includes a port for supplying test liquid to the liquid-absorbent article while the absorbent article is maintained in the compressed condition.

10. A pressure cell as defined in claim 8, wherein said plate includes a port for receiving a probe of an instrument for measuring a liquid-absorbent characteristic of the liquid-absorbent article.

11. A pressure cell as defined in claim 1, further comprising:
   an upper generally rigid and horizontally extending plate, said upper plate constituting said abutment member; and
   a lower generally rigid and horizontally extending plate vertically spaced apart with relation to said upper plate, said variable volume chamber being mounted between said plates.

12. A pressure cell as defined in claim 11, wherein said plates are vertically adjustable for varying a spacing therebetween.

13. A method for conditioning a liquid-absorbent article by the application of pressure to the liquid-absorbent article during a liquid-absorbency test, said method comprising the steps of:
   placing the liquid-absorbent article between an abutment member and a flexible membrane forming a wall of an inflatable bag;
   injecting pressurized fluid in said bag to cause said flexible membrane to compress the liquid-absorbent article while conforming thereto, whereby allowing to conduct a liquid-absorbency test on the liquid-absorbent article while maintaining the liquid-absorbent article in a compressed condition between said flexible membrane and said abutment member.

14. A method as defined in claim 13, comprising pumping air in said inflatable bag for inflating said inflatable bag.

* * * * *